United States Patent [19]
Wu

[11] Patent Number: 6,002,012
[45] Date of Patent: Dec. 14, 1999

[54] PROCESS FOR THE PREPARATION OF [(5,6-DICARBOXY-3-PYRIDYL) METHYL] AMMONIUM HALIDES

[75] Inventor: Wen-Xue Wu, Mercer, N.J.

[73] Assignee: American Cyanamid Company, Madison, N.J.

[21] Appl. No.: 09/045,203

[22] Filed: Mar. 20, 1998

Related U.S. Application Data

[63] Continuation of application No. 08/661,206, Jun. 10, 1996, abandoned.

[51] Int. Cl.$^6$ ..................... C07D 213/807; C07D 401/04
[52] U.S. Cl. ..................... 546/274.1; 546/287; 546/310; 546/321
[58] Field of Search ................... 546/321, 274.1, 546/587, 310

[56] References Cited

U.S. PATENT DOCUMENTS

| | | | |
|---|---|---|---|
| 4,816,588 | 3/1989 | Rieker et al. | 546/321 |
| 5,288,866 | 2/1994 | Strong | 544/215 |
| 5,369,022 | 11/1994 | Newhouse et al. | 435/172.1 |
| 5,378,843 | 1/1995 | Strong | 544/215 |
| 5,625,068 | 4/1997 | Strong | 546/171 |
| 5,633,380 | 5/1997 | Wu | 546/174 |

FOREIGN PATENT DOCUMENTS

| | | |
|---|---|---|
| 0 220 518 B1 | 2/1991 | European Pat. Off. |
| 0 331 899-A2 | 2/1989 | United Kingdom |
| 0 388 619-A1 | 3/1990 | United Kingdom |

OTHER PUBLICATIONS

March, Advanced Organic Chemistry, 4th Edition, p. 1016, 1992.
Leete et al., Canadian Journal of Chemistry, vol. 31, No. 9, pp. 775–784, Sept. 1953.
Wuest et al., Recueil, vol. 78, pp. 226–243, 1959.

*Primary Examiner*—Richard L. Raymond
*Attorney, Agent, or Firm*—Barbara L. Renda

[57] ABSTRACT

There is provided a process for the preparation of [(5,6-dicarboxy-3-pyridyl)methyl]ammonium halides having the structural formula I

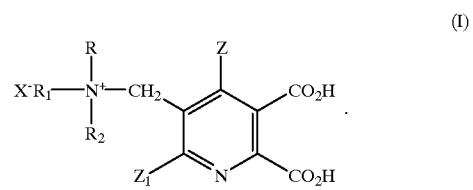

The [(5,6-dicarboxy-3-pyridyl)methyl]ammonium halides are useful as intermediates in the preparation of herbicidal 5-(alkoxymethyl)-2-(2-imidazolin-2-yl)-nicotinic acids, esters and salts.

10 Claims, No Drawings

PROCESS FOR THE PREPARATION OF [(5,6-DICARBOXY-3-PYRIDYL) METHYL] AMMONIUM HALIDES

This is a continuation of application(s) Ser. No. 08/661,206 filed on Jun. 10, 1996, now abandoned the entire disclosure of which is hereby incorporated by reference.

BACKGROUND OF THE INVENTION

[(5,6-Dicarboxy-3-pyridyl)methyl]ammonium halides are useful as intermediates in the preparation of herbicidal 5-(alkoxymethyl)-2-(2-imidazolin-2-yl)nicotinic acids, esters and salts. A process for converting 5-methyl-2,3-pyridinedicarboxylic acid derivatives into [(5,6-dicarboxy-3-pyridyl)methyl]-ammonium halides is described in U.S. Ser. No. 5,378,843. Although the process of that patent is useful, there is ongoing research to discover new processes for preparing [(5,6-dicarboxy-3-pyridyl)methyl]ammonium halides.

It is, therefore, an object of the present invention to provide an effective and efficient process for the preparation of [(5,6-dicarboxy-3-pyridyl)methyl]ammonium halides.

SUMMARY OF THE INVENTION

The present invention provides an effective and efficient process for the preparation of a [(5,6-dicarboxy-3-pyridyl)methyl]ammonium halide having the structural formula I

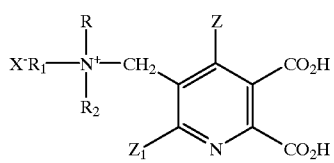

(I)

wherein
  $R$, $R_1$ and $R_2$ are each independently $C_1$–$C_4$alkyl, and when taken together, R and $R_1$ may form a 5- or 6-membered ring optionally interrupted by O, S or $NR_3$;
  $R_3$ is $C_1$–$C_4$alkyl;
  X is Cl, Br or I;
  Z is hydrogen or halogen; and
  $Z_1$ is hydrogen, halogen, cyano or nitro, which process comprises oxidizing a substituted (3-quinolylmethyl) ammonium halide having the structural formula II

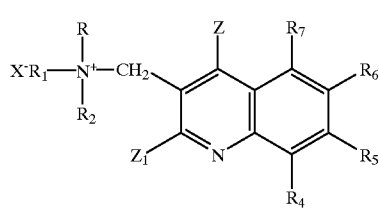

(II)

wherein
  $R$, $R_1$, $R_2$, X, Z and $Z_1$ are as described for formula I above;
  $R_4$, $R_5$, $R_6$ and $R_7$ are each independently hydrogen, hydroxy, nitro, $OC(O)R_8$, halogen, $NR_9R_{10}$, $C_1$–$C_4$alkoxy, $SO_3H$, $SO_2Cl$ or SH, with the proviso that one of $R_4$, $R_5$, $R_6$ and $R_7$ is other than hydrogen or halogen;
  $R_8$ is $C_1$–$C_4$alkyl, $C_1$–$C_4$alkoxy, phenyl or $NR_{11}R_{12}$;
  $R_9$, $R_{10}$, $R_{11}$ and $R_{12}$ are each independently hydrogen, $C_1$–$C_4$alkyl or phenyl;
  the N-oxides thereof; and
  the acid addition salts thereof, with hydrogen peroxide in the presence of aqueous base.

DETAILED DESCRIPTION OF THE INVENTION

In a preferred embodiment of the present invention, a substituted (3-quinolylmethyl)ammonium halide represented by formula II is oxidized with at least about 8 molar equivalents of hydrogen peroxide in the presence of at least about 1 molar equivalent, preferably about 4 to 10 molar equivalents, of an aqueous base, preferably in a temperature range of about 50° C. to 100° C., more preferably about 75° C. to 95° C.

Advantageously, it has been found that [(5,6-dicarboxy-3-pyridyl)methyl]ammonium halides are obtained in high yield and purity by the effective and efficient process of the present invention.

The product [(5,6-dicarboxy-3-pyridyl)methyl]-ammonium halides may be isolated by acidifying the reaction mixture with a mineral acid and collecting the resultant formula I product by standard procedures. Alternatively, the reaction mixture may be integrated into the process used to prepare the final herbicidal agent without isolating the formula I compound.

Exemplary of halogen hereinabove for Z, $Z_1$, $R_4$, $R_5$, $R_6$ and $R_7$ are fluorine, chlorine, bromine and iodine with chlorine being preferred.

Aqueous bases suitable for use in the process of the present invention include alkali metal hydroxides such as sodium hydroxide and potassium hydroxide, alkaline earth metal hydroxides such as calcium hydroxide, alkali metal carbonates such as sodium carbonate and potassium carbonate, alkaline earth metal carbonates such as calcium carbonate, and mixtures thereof. Preferred aqueous bases include aqueous sodium hydroxide and aqueous potassium hydroxide.

Advantageously, the formula II substituted (3-quinolylmethyl)ammonium halides are highly soluble in the aqueous base. In general, base concentrations from about 35% to 65% on a weight basis are preferred, with base concentrations from about 40% to 60% being more preferred. In the past, certain quinolines have been oxidized with hydrogen peroxide in the presence of aqueous bases having concentrations of up to about 35% on a weight basis (see, e.g., U.S. Pat. No. 4,816,588). However, the use of a more concentrated aqueous base is desirable because it reduces the amount of aqueous waste produced. Another advantage of the process of this invention is that water miscible co-solvents are not required because the substituted (3-quinolylmethyl)ammonium halides are highly soluble in the aqueous base.

A minimum of 8 molar equivalents of hydrogen peroxide is required to completely oxidize a formula II substituted (3-quinolylmethyl)ammonium halide. Preferably, about 8 to 60 molar equivalents of 30% to 50% aqueous hydrogen peroxide, more preferably about 8 to 40 molar equivalents of 30% to 50% aqueous hydrogen peroxide, are used to oxidize the formula II compound.

In a preferred process of the present invention,
  $R$, $R_1$ and $R_2$ are each independently $C_1$–$C_4$alkyl;
  X is Cl or Br;

Z and $Z_1$ are hydrogen;

at least one of $R_4$, $R_5$, $R_6$ and $R_7$ is hydroxy, nitro or $OC(O)R_8$; and $R_8$ is $C_1$–$C_4$alkyl, $C_1$–$C_4$alkoxy or phenyl.

In a more preferred process of the present invention,

R, $R_1$ and $R_2$ are methyl;

X is Br;

$R_5$, $R_6$, $R_7$, Z and $Z_1$ are hydrogen;

$R_4$ is hydroxy, nitro or $OC(O)R_8$; and $R_8$ is $C_1$–$C_4$alkyl or $C_1$–$C_4$alkoxy.

Substituted (3-quinolylmethyl)ammonium halides of formula II may be prepared by halogenating a substituted 3-methylquinoline of formula III with a halogenating agent in the presence of a solvent and optionally in the presence of a catalytic amount of a radical initiator to form a substituted 3-halomethylquinoline of formula IV and reacting the formula IV compound with at least about one molar equivalent of an amine of formula V in the presence of a solvent. The reaction scheme is shown below in Flow Diagram I.

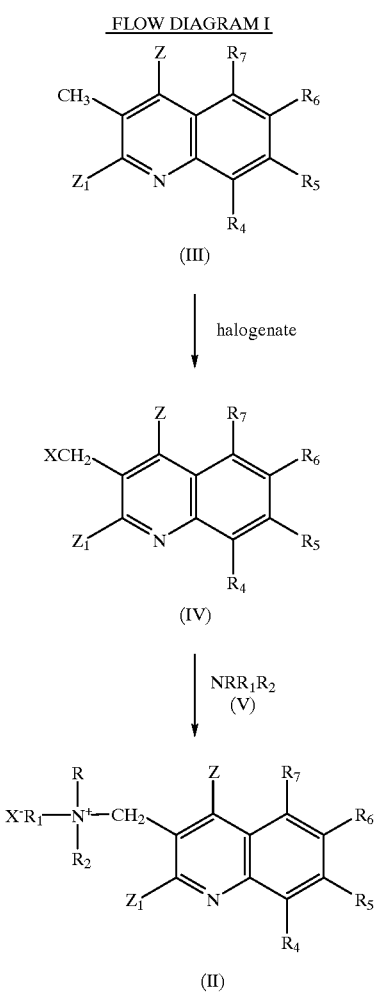

The present invention also provides a process for the preparation of a herbicidal 5-(alkoxymethyl)-2-(2-imidazolin-2-yl)-nicotinic acid, ester and salt compound having the formula

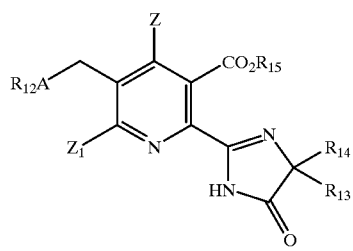

wherein

Z and $Z_1$ are as defined above;

A is O or S;

$R_{12}$ is $C_1$–$C_4$ alkyl optionally substituted with phenyl optionally substituted with one to three $C_1$–$C_4$ alkyl groups or halogen atoms, or phenyl optionally substituted with one to three $C_1$–$C_4$ alkyl groups or halogen atoms;

$R_{13}$ is $C_1$–$C_4$ alkyl;

$R_{14}$ is $C_1$–$C_4$ alkyl, $C_3$–$C_6$ cycloalkyl or $R_{13}$ and $R_{14}$ when taken together with the atom to which they are attached, represent a $C_3$–$C_6$ cycloalkyl group optionally substituted with methyl and $R_{15}$ is hydrogen, diloweralkylimino, $C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, lower alkylphenyl, lower alkoxyphenyl, nitrophenyl, carboxyl, loweralkoxycarbonyl, cyano or triloweralkylammonium;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups; or a cation preferably selected from the group consisting of alkali metals, alkaline earth metals, manganese, copper, iron, zinc, cobalt, lead, silver, nickel, ammonium and organic ammonium; and when $R_{13}$ and $R_{14}$ represent different substituents, the optical isomers thereof;

which process comprises:

(a) preparing a compound having the formula I

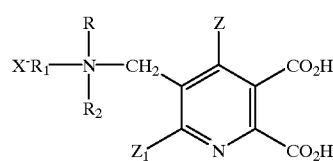

wherein Z, $Z_1$, R, $R_1$, $R_2$ and X are as defined above by a process as defined above; and (b) converting the said compound having formula I into the compound having the formula VI.

The term "lower" as used above in relation to alkyl and alkoxy groups means that the alkyl or alkoxy group contains 1 to 6, preferably 1 to 4, carbon atoms.

The conversion of the compound having formula I into the compound having formula VI may be carried out in a variety of ways. One may plan routes by combining reactions known for the conversion of one carboxylic acid derivative into another.

Methods that may be used to create the imidazolinone herbicides are illustrated in the book "The Imidazolinone Herbicides" edited by D. L. Shaner and S. L. O'Connor, published 1991 by CRC Press, Boca Raton, Fla. with particular reference to Chapter 2 entitled "Synthesis of the Imidazolinone Herbicides", pages 8–14 and the references cited therein. The following patent literature references also illustrate the methods that may be used to convert the carboxylic acid derivatives into imidazolinone final products:

U.S. Pat. Nos. 5,378,843; 5,371,229; 5,520,694;
5,110,930; 5,122,608; 5,206,368; 4,925,944;
4,921,961; 4,959,476; 5,103,009; 4,816,588;
4,757,146; 4,798,619; 4,766,218; 5,001,254;
15,021,078; 4,723,011; 4,709,036; 4,658,030;
4,608,079; 4,719,303; 4,562,257; 4,518,780;
4,4474,962; 4,623,726; 4,750,978; 4,638,068;
4,439,607; 4,459,408; 4,459,409; 4,460,776;
4,125,727 and 4,758,667, and European Patent Application Nos. EP-A-0-041,623; EP-A-0-331,899 and EP-A-0-388,619.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

Preparation of [(5.6-Dicarboxy-3-pyridyl)methyl]trimethylammonium bromide

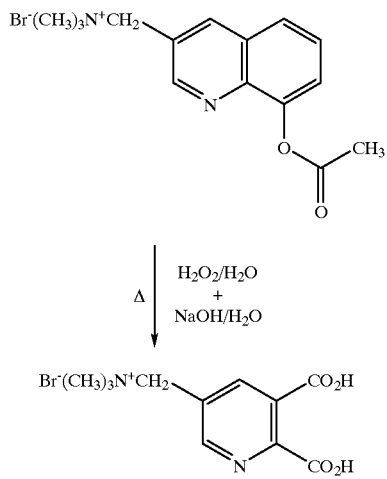

Hydrogen peroxide solution (20 g, 30 wt/wt %, 12 equivalents) is added to a stirred solution of [(8-acetoxy-3-quinolyl)methyl]trimethylammonium bromide (5.0 g, 14.7 mmol) and sodium hydroxide solution (9.4 g, 50 wt/wt %, 8 equivalents) at 85° to 90° C. over 15 minutes. The resultant reaction mixture is stirred at 85° to 90° C. for 90 minutes, treated with additional hydrogen peroxide solution (26 g, 30 wt/wt %, 15.6 equivalents) at 85° C. over 30 minutes, and stirred at 85° to 90° C. for one hour. LC analysis of the final reaction mixture indicates that the title product is produced in 80% yield.

EXAMPLES 2–4

Using essentially the same procedure as described in Example 1, but using various [(8-substituted-3-quinolyl)methyl]trimethylammonium bromides, [(5,6-dicarboxy-3-pyridyl)methyl]trimethylammonium bromide is produced in the yields shown in Table I.

TABLE I

Preparation of [(5,6-Dicarboxy-3-pyridyl)methyl]trimethylammonium bromide

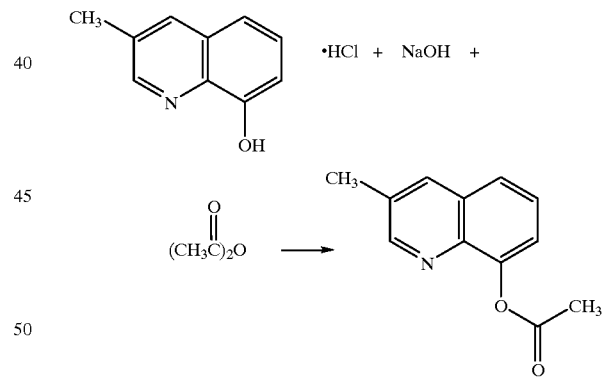

| Example | $R_4$ | Equivalents of 50 wt/wt % NaOH Solution | Equivalents of 30 wt/wt % $H_2O_2$ Solution | Hours Stirred at 85° to 90° C. | % Yield[1] of I |
|---|---|---|---|---|---|
| 2 | OH | 8 | 38 | 1.83 | 86 |
| 3 | $OCO_2CH_3$ | 9.8 | 58 | 1.75 | 83 |
| 4 | $NO_2$ | 8 | 32 | 2.58 | 45 |

[1]Determined by LC analysis of reaction mixture

EXAMPLE 5

Preparation of 8-Acetoxy-3-methylquinoline

A mixture of the hydrochloride salt of 8-hydroxy-3-methylquinoline (200 g, 1.02 mol) and sodium hydroxide (102 g, 2.55 mol) in water (1,000 mL) is treated with acetic anhydride (208 g, 2.04 mol) at 0° to 10° C. over 1 hour and stirred at room temperature for 1 hour. An additional portion of acetic anhydride (50 g, 0.49 mol) is added and the resultant mixture is stirred for one hour, treated with saturated sodium bicarbonate solution (100 mL) and filtered to obtain a solid. The solid is washed with water, dried at 60° C. in a vacuum oven and recrystallized form an ethyl acetate/heptane solution to give the title product as white needles (168.5 g, 82% yield).

EXAMPLE 6

Preparation of 8-Benzoyloxy-3-methylquinoline

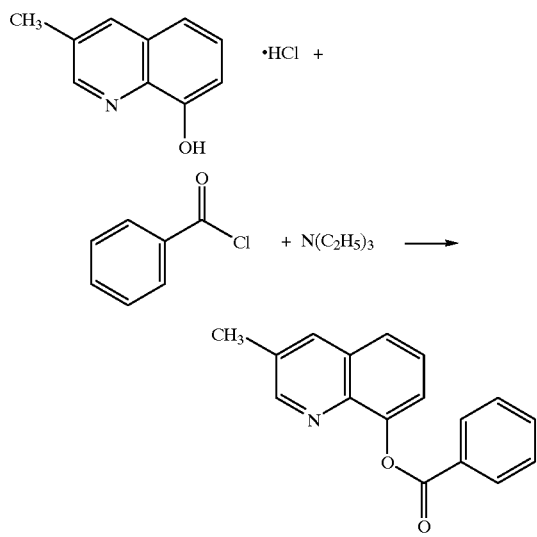

A mixture of the hydrochloride salt of 8-hydroxy-3-methylquinoline (10 g, 0.051 mol) and triethylamine (15.5 g, 0.15 mol) in methylene chloride (100 mL) is treated with benzoyl chloride (10.8 g, 0.077 mol) at 0° to 10° C. over 1 hour, stirred at room temperature for three hours and diluted with water. The phases are separated, and the organic phase is washed with water, dried over anhydrous magnesium sulfate and concentrated in vacuo to obtain solid. The solid is recrystallized from a heptane/toluene solution to give the title product as pale yellow crystals (8.8 g, 65% yield).

EXAMPLE 7

Preparation of [(8-Acetoxy-3-quinolyl)methyl]trimethylammonium bromide

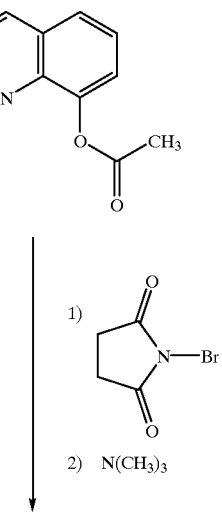

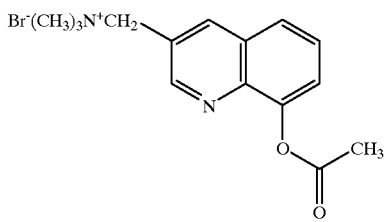

A solution of 8-acetoxy-3-methylquinoline (168.5 g, 0.84 mol), N-bromosuccinimide (177.9 g, 1.00 mol) and 2,2'-azobisisobutyronitrile (6.7 g, 0.04 mol) in chlorobenzene (1,675 mL) is purged with nitrogen, heated at 80° to 90° C. under nitrogen for 2 hours, cooled to room temperature and filtered. A mixture of the filtrate in acetone (700 mL) is treated with trimethylamine (75.4 g, 1.28 mol) at 0° to 5° C., stirred at 5° to 10° C. for 30 minutes, stirred at room temperature for 1 hour and filtered to obtain a solid. The solid is washed with acetone and dried at 60° C. in a vacuum oven to give the title product as a white solid (180 g, 63% overall yield).

Using essentially the same procedure, but using various 8-substituted-3-methylquinolines, the following compounds are obtained.

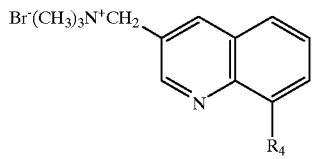

| $R_4$ |
| --- |
| $OC(O)C_6H_5$ |
| $OC(O)OCH_3$ |
| $NO_2$ |

EXAMPLE 8

Preparation of [(8-Hydroxy-3-quinolyl)methyl]trimethylammonium bromide

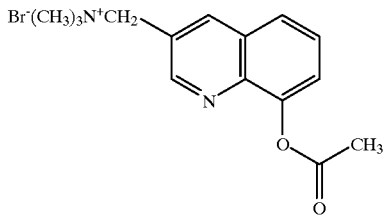

A solution of [(8-acetoxy-3-quinolyl)methyl]trimethylammonium bromide (5.0 g, 14.7 mmol) in methanol is refluxed for 13.5 hours and concentrated in vacuo to obtain a residue. The residue is dried in a vacuum oven at 60° C. to give the title product as an off-white solid (4.4 g, 100% yield).

I claim:

1. A process for the preparation of a [(5,6-dicarboxy-3-pyridyl)methyl]ammonium halide having the structural formula I

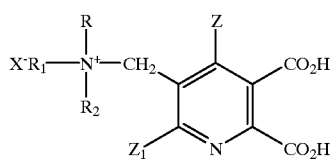

wherein

R, $R_1$ and $R_2$ are each independently $C_1$–$C_4$alkyl, and when taken together, R and $R_1$ may form a 5- or 6-membered ring optionally interrupted by O, S or $NR_3$;

$R_3$ is $C_1$–$C_4$alkyl;

X is Cl, Br or I;

Z is hydrogen or halogen; and $Z_1$ is hydrogen, halogen, cyano or nitro, which process comprises oxidizing a substituted (3-quinolylmethyl) ammonium halide having the structural formula II

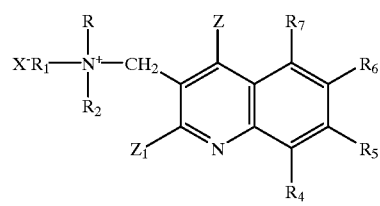

wherein

R, $R_1$, $R_2$, X, Z and $Z_1$ are as described for formula I above;

$R_4$, $R_5$, $R_6$ and $R_7$ are each independently hydrogen, hydroxy, nitro, $OC(O)R_8$, halogen, $NR_9R_{10}$, $C_1$–$C_4$alkoxy, $SO_3H$, $SO_2Cl$ or SH, with the proviso that one of $R_4$, $R_5$, $R_6$ and $R_7$ is other than hydrogen or halogen;

$R_8$ is $C_1$–$C_4$alkyl, $C_1$–$C_4$alkoxy, phenyl or $NR_{11}R_{12}$;

$R_9$, $R_{10}$, $R_{11}$, and $R_{12}$ are each independently hydrogen, $C_1$–$C_4$alkyl or phenyl;

the N-oxides thereof; and the acid addition salts thereof, with hydrogen peroxide in the presence of aqueous base.

2. The process according to claim 1 wherein

R, $R_1$ and $R_2$ are each independently $C_1$–$C_4$alkyl;

X is Cl or Br;

Z and $Z_1$ are hydrogen;

at least one of $R_4$, $R_5$, $R_6$ and $R_7$ is hydroxy, nitro or $OC(O)R_8$; and $R_8$ is $C_1$–$C_4$alkyl, $C_1$–$C_4$alkoxy or phenyl.

3. The process according to claim 2 wherein

R, $R_1$ and $R_2$ are methyl;

X is Br;

$R_5$, $R_6$, $R_7$, Z and $Z_1$ are hydrogen;

$R_4$ is hydroxy, nitro or $OC(O)R_8$; and $R_8$ is $C_1$–$C_4$alkyl or $C_1$–$C_4$alkoxy.

4. The process according to claim 1 wherein the hydrogen peroxide is present in an amount from about 8 to 60 molar equivalents relative to the formula II substituted (3-quinolylmethyl)ammonium halide.

5. The process according to claim 1 wherein the aqueous base is present in an amount of at least about one molar equivalent relative to the formula II substituted (3-quinolylmethyl)ammonium halide.

6. The process according to claim 5 wherein the aqueous base is present in an amount from about 4 to 10 molar equivalents.

7. The process according to claim 1 wherein the aqueous base is aqueous sodium hydroxide or aqueous potassium hydroxide.

8. The process according to claim 1 wherein the formula II substituted (3-quinolylmethyl)ammonium halide is oxidized with hydrogen peroxide in the presence of an aqueous base at a temperature range of about 50° C. to 100° C.

9. The process according to claim 8 wherein the temperature is about 75° C. to 95° C.

10. A process for the preparation of a herbicidal imidazolinone compound having the formula VI

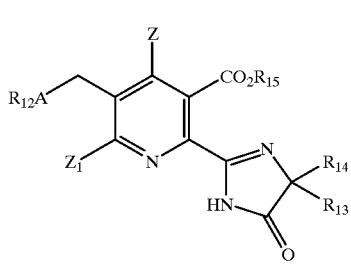

wherein

Z and $Z_1$ are as defined in claim 1;

A is O or S;

$R_{12}$ is $C_1$–$C_4$ alkyl optionally substituted with phenyl optionally substituted with one to three $C_1$–$C_4$ alkyl groups or halogen atoms, or phenyl optionally substituted with one to three $C_1$–$C_4$ alkyl groups or halogen atoms;

$R_{13}$ is $C_1$–$C_4$ alkyl;

$R_{14}$ is $C_1$–$C_4$ alkyl, $C_3$–$C_6$ cycloalkyl or $R_{13}$ and $R_{14}$ when taken together with the atom to which they are attached, represent a $C_3$–$C_6$ cycloalkyl group optionally substituted with methyl and $R_{15}$ is hydrogen, diloweralkylimino, $C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, lower alkylphenyl, lower alkoxyphenyl, nitrophenyl, carboxyl, loweralkoxycarbonyl, cyano or triloweralkylammonium;

$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups; or a cation and when $R_{13}$ and $R_{14}$ represent different substituents, the optical isomers thereof;

which process comprises:

(a) preparing a compound having the formula I

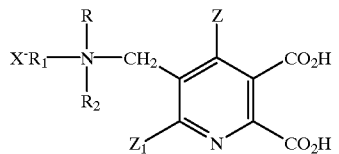

wherein Z, $Z_1$, R, $R_1$, $R_2$ and X are defined in claim 1 by a process as claimed in claim 1; and (b) converting the compound having formula I into the compound having the formula VI.

\* \* \* \* \*